United States Patent [19]

Goldberg et al.

[11] Patent Number: 5,234,409
[45] Date of Patent: Aug. 10, 1993

[54] FEMALE INCONTINENCE CONTROL DEVICE AND METHOD

[75] Inventors: Jay R. Goldberg, Libertyville; Rebecca Y. Chin, Mundelein, both of Ill.; Carl B. Barwick, Caledonia; Robert E. Trick, Racine, both of Wis.

[73] Assignee: Cabot Technology Corporation, Wilmington, Del.

[21] Appl. No.: 973,225

[22] Filed: Nov. 9, 1992

Related U.S. Application Data

[63] Continuation of Ser. No. 376,717, Jul. 7, 1989, abandoned.

[51] Int. Cl.$^5$ .................. A61M 29/00; A61F 5/44; A61F 2/02
[52] U.S. Cl. .................. 604/96; 604/249; 604/329; 600/30; 128/DIG. 25
[58] Field of Search .................. 600/29–31; 128/DIG. 25; 604/96, 99, 102, 246, 249, 247, 327–331

[56] References Cited

U.S. PATENT DOCUMENTS

| | | | |
|---|---|---|---|
| 2,784,716 | 3/1957 | Broman | 604/249 X |
| 2,964,292 | 12/1960 | Noir | 604/249 X |
| 3,354,898 | 11/1967 | Barnes . | |
| 3,399,677 | 9/1968 | Gould et al. | 604/99 |
| 3,419,008 | 12/1968 | Plishner . | |
| 3,503,400 | 3/1970 | Ostagen et al. | 604/249 |
| 3,570,484 | 3/1971 | Steer et al. | 604/249 |
| 3,642,004 | 2/1972 | Osthagen et al. . | |
| 3,731,360 | 5/1973 | Stone, Jr. . | |
| 3,731,670 | 5/1973 | Loe . | |
| 3,812,841 | 5/1974 | Isaacson | 604/249 X |
| 3,841,304 | 10/1974 | Jones | 600/29 |
| 3,851,668 | 12/1974 | Benjamin | 137/625.3 |
| 4,089,337 | 5/1978 | Kronner | 604/96 |
| 4,563,183 | 1/1988 | Barrodale et al. . | |
| 4,723,946 | 2/1988 | Kay | 604/267 |
| 4,813,935 | 3/1989 | Haber et al. | 604/99 |
| 4,850,963 | 7/1989 | Sparks et al. . | |
| 4,932,938 | 6/1990 | Goldberg et al. | 604/96 |
| 4,968,294 | 11/1990 | Salama | 600/30 |
| 5,112,306 | 5/1992 | Burton et al. | 604/101 |

FOREIGN PATENT DOCUMENTS

| | | |
|---|---|---|
| 21339 | 7/1983 | Australia . |
| 76349 | 4/1987 | Australia . |
| 2537506 | 3/1977 | Fed. Rep. of Germany . |
| 1194358 | 6/1970 | United Kingdom . |
| 2219943 | 12/1989 | United Kingdom . |

Primary Examiner—John D. Yasko
Assistant Examiner—Adam Cermak
Attorney, Agent, or Firm—Austin R. Miller

[57] ABSTRACT

A female incontinence control device includes a conduit having inlet and outlet openings for receiving, conducting and discharging urinary fluid. The device also includes structure for holding the conduit in position relative to the urethra such that the inlet opening is adapted to receive substantially all of the urinary fluids which drain from the bladder, and the outlet opening of the conduit is positioned outside the urethra. In one embodiment of the invention, the device can be entirely contained within the labia majora. In other embodiments of the invention the device extends through the urethra to the bladder. In all embodiments of the invention a drainage control valve is positioned within the conduit for location intermediate the urethral orifice and the labia majora for manual actuation to selectively control urinary flow through the conduit. The method of controlling female incontinence includes the steps of providing and positioning a conduit to receive the urinary fluid and manually actuating a valve in the conduit by squeezing the conduit, to allow accumulated urinary fluids to be drained from the urinary tract.

23 Claims, 4 Drawing Sheets

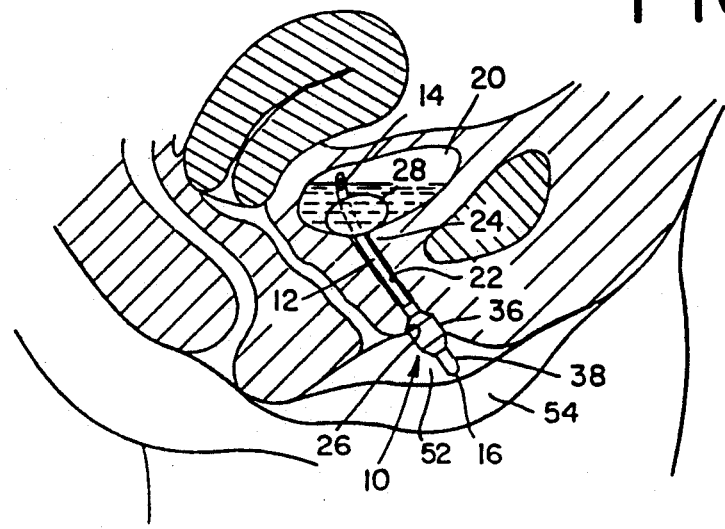
FIG.1
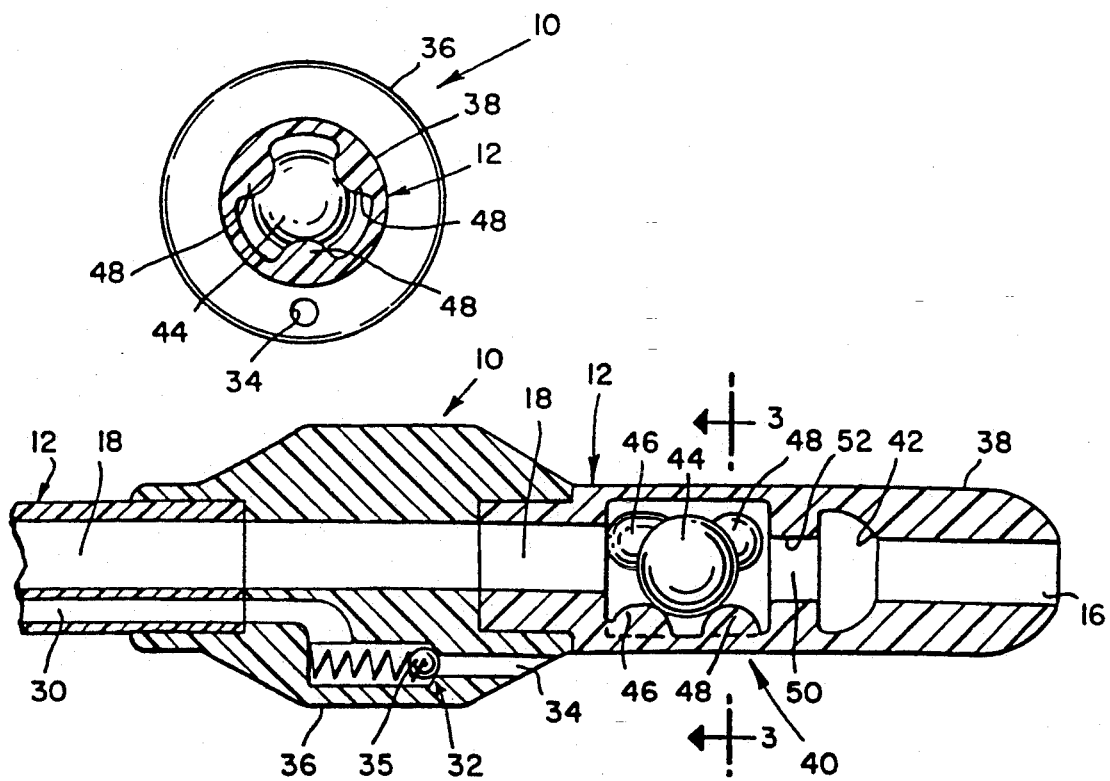
FIG.3
FIG.2

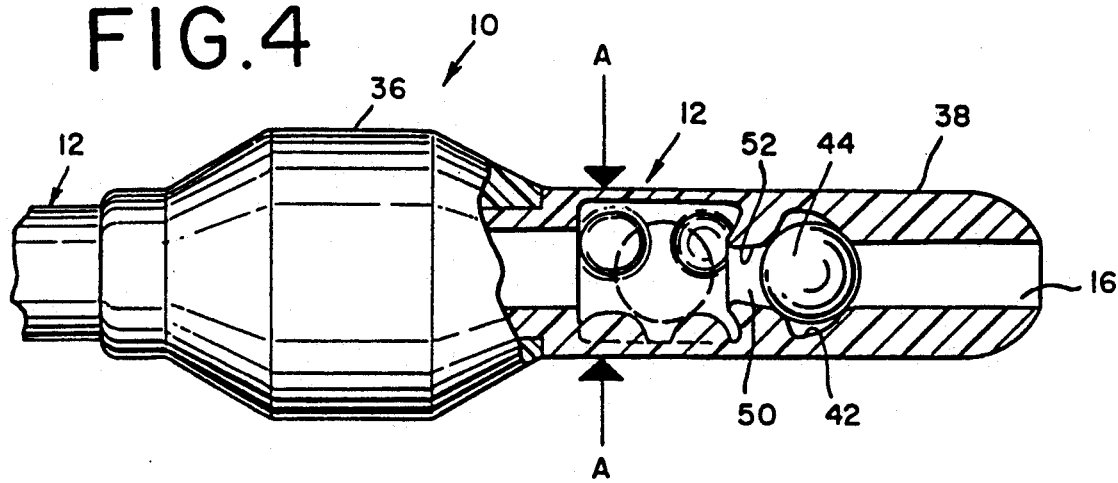
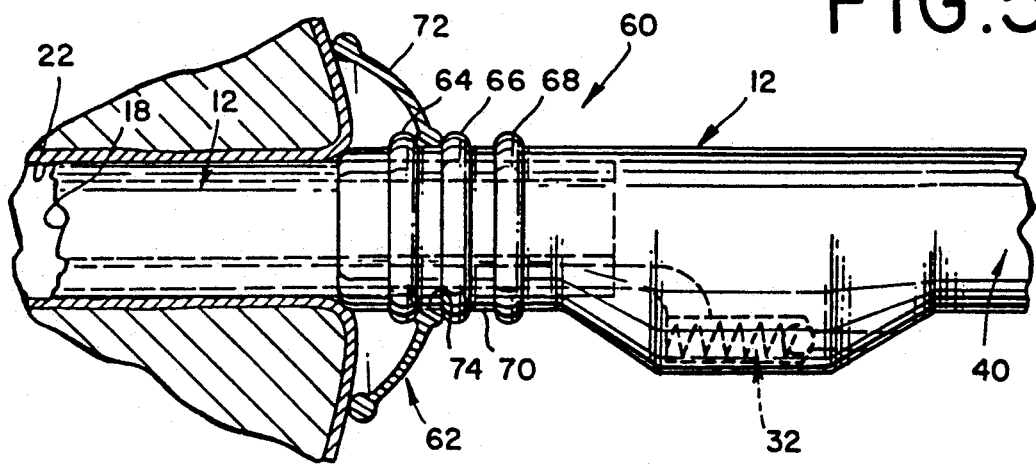
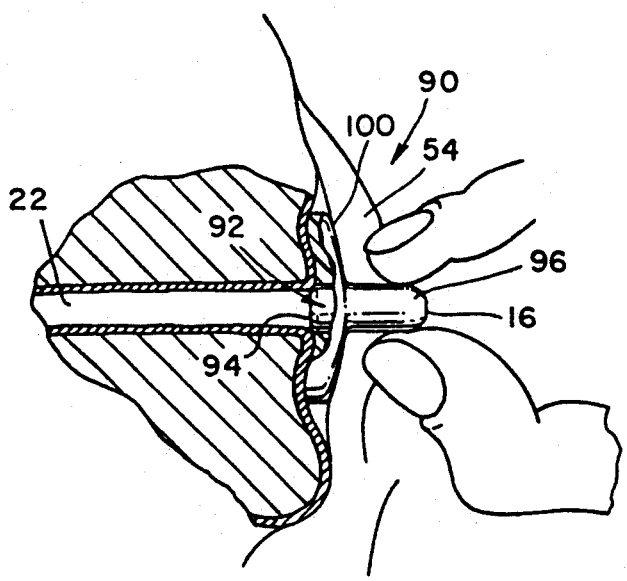

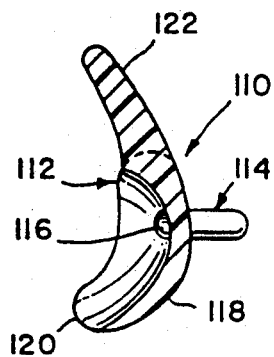
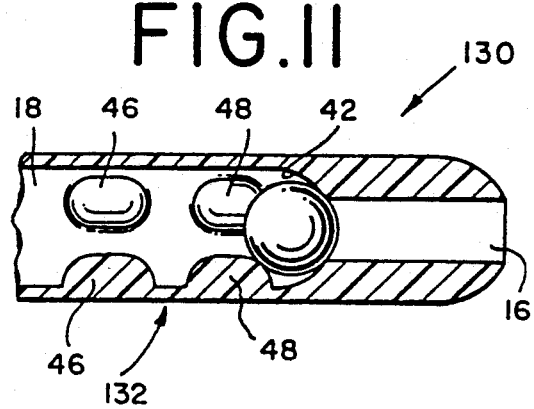
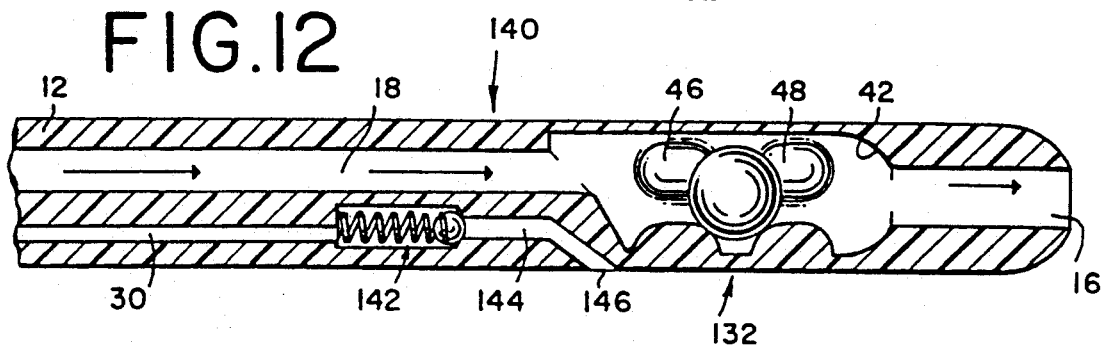
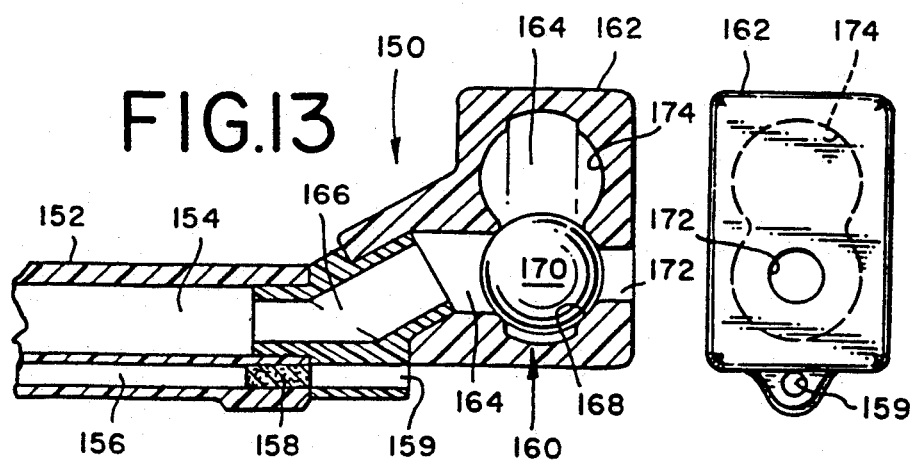

FEMALE INCONTINENCE CONTROL DEVICE AND METHOD

This application is a continuation of application Ser. No. 07/376,717, filed Jul. 7, 1989 now abandoned.

BACKGROUND OF THE INVENTION

This invention relates to devices and methods for controlling female incontinence and more particularly to a novel female incontinence control device that employs a manually actuatable valve for controlling urinary discharge, and a novel method of controlling urinary discharge.

Urinary incontinence, or the loss of bladder control, is a problem that many women cope with on a daily basis. Female urinary incontinence often results from muscle weakness, post-operative surgical damage to the urinary sphincter or a variety of other debilitating problems. Thus far there have been no satisfactory surgical procedures for correcting incontinence to the extent that bladder control is substantially restored.

Some known devices that deal with the problem of female incontinence allow the bladder to continuously drain into a collection bag and thus do not enable the user to adequately control urinary discharge. Other known devices which are directed to the problem of female incontinence attempt some form of drainage control and include catheters, draining probes and dilators, such as shown in U.S. Pat. Nos. 4,194,508; 4,198,979 and 4,563,183. Generally such known devices also include an external fluid collection system fastened to a portion of the users body. Unfortunately, a collection system that is carried by a user inhibits the users activities and can provide a path for bacterial infection.

Not only are catheters, collection bags, and absorbent pads awkward to use in dealing with incontinence they are often a potential source of embarrassment to the user. Attempts to address such problems as lack of control, bulkiness, discomfort, embarrassment and inhibition of activity have led to the development of valved incontinence control devices, which eliminate the need for external collection systems and allow the user to manually control the flow of urinary fluids from the urinary tract. Examples of such devices are shown in U.S. Pat. Nos. 3,503,400, 3,939,821 and 4,024,855.

In U.S. Pat. No. 3,503,400 a manually controllable valve is positioned within the urethra near the bladder. The valve is operated by a control cable that passes through the urethra to permit exterior access by the user. Such an arrangement, although permitting positive drainage control, provides a potential path for bacterial infection of the urinary tract, and can also cause embarrassment to the user due to the fact that the control cable must extend outside the user's body.

In U.S. Pat. Nos. 3,939,821 and 4,024,855 magnetic valve members are surgically implanted about the urethra of the user and require external actuating means to cause the valve to operate. Such devices necessitate surgical implantation of the magnetic valve members, and require the user to be equipped with an external actuating member in order to actuate the valve to accomplish urinary discharge.

It is thus desirable to provide a female incontinence control device that is manually actuatable by the user to control urinary discharge, is relatively comfortable to use and does not unduly impede normal activity of the user.

OBJECTS AND SUMMARY OF THE INVENTION

Among the several objects of the invention may be noted the provision of the novel female incontinence device having a manually actuatable control valve for controlling urinary discharge, a novel female incontinence device which is substantially entirely contained within the body of the user, a novel female incontinence device which can be easily removed and reinstalled, a novel female incontinence device which can be operated by manual pressure, a novel female incontinence device which is adjustable for comfortable installation, a novel female incontinence device which can be optionally affixed in the urethral passage, a novel female incontinence device which effectively prevents urinary discharge when such discharge is not desired and permits such discharge upon simple manipulation of the device, and a novel method of controlling female incontinence.

Other objects and features of the invention will be in part apparent and in part pointed out hereinafter.

In accordance with the invention, the female incontinence control device includes a conduit having inlet and outlet openings for receiving, conducting and discharging urinary fluid. The device also includes structure for holding the conduit in a selected position relative to the urethra such that the inlet opening is adapted to receive urinary fluids that drain from the bladder for discharge through the outlet opening.

A discharge control valve provided within the conduit is positioned either intermediate the urethra and the labia majora or distal to the labia majora. The valve is manually actuatable for selectively controlling the flow of urinary fluids through the conduit. Affixation structure is provided on the device to prevent inadvertent removal of the conduit from the labia majora and to prevent migration of the control valve portion of the device into the urethra.

The entire valve can be accommodated between the urethral orifice and the labia majora, or distal to the labia majora. Thus the valve can be manually actuated yet does not inhibit general physical activity.

In several embodiments of the invention the device extends proximally from the urethral opening into the bladder and in other embodiments, substantially the entire structure of the device is physically disposed inwardly of the labia majora, or distal to the labia majora.

In one embodiment of the invention the device is adjustable in length to correspond with the length of the urethral tract. In other embodiments of the device the length of the urethral tract does not bear upon the structure of the device since the device does not extend the full length of the urethra.

Female incontinence is thus controlled by providing a conduit with inlet and outlet openings and a valve for controlling flow of urine past the outlet opening. The conduit is positioned such that at least the inlet opening and the valve portion of the conduit are located within the labia majora. The valve may be located distal to the labia majora for easier access. The inlet opening of the conduit preferably sealingly engages the urinary tract to enable the conduit to receive substantially all of the urinary fluids which drain from the bladder. Thus the control valve, when closed, permits accumulation of urinary fluids in the urinary tract and, when open, allows the urinary fluids to pass through the conduit for discharge from the outlet opening. Selective manual opening of the valve thus allows the accumulated urinary fluids to be drained from the urinary tract at the convenience of and within the control of the user. The valve is manually closed when urinary discharge is completed. The conduit can be positioned within the labia majora, or it can extend through the urinary tract to the bladder.

The invention accordingly comprises the constructions and method hereinafter described, the scope of the invention being indicated in the claims.

DESCRIPTION OF THE DRAWINGS

In the accompanying drawings,

FIG. 1 is a simplified schematic view of an incontinence control device incorporating one embodiment of the invention in an operating position within the female anatomy;

FIG. 2 is an enlarged fragmentary sectional view of a distal end portion thereof showing a valve means therein in an open position;

FIG. 3 is a sectional elevational view taken on the line 3—3 of FIG. 2;

FIG. 4 is a view similar to FIG. 2 showing the valve means in a closed position;

FIGS. 5-8 are enlarged fragmentary views of further embodiments of the invention in operational position within the female anatomy;

FIG. 10 is an elevational view of the FIG. 8 embodiment;

FIGS. 11 and 12 are enlarged, fragmentary sectional views of further embodiments of the invention;

FIG. 13 is an enlarged, fragmentary sectional view of another embodiment of the invention; and, FIG. 14 is an end view of the FIG. 8 embodiment.

Corresponding reference characters indicate corresponding parts throughout the several views of the drawings.

DETAILED DESCRIPTION OF THE INVENTION

Figure 7:
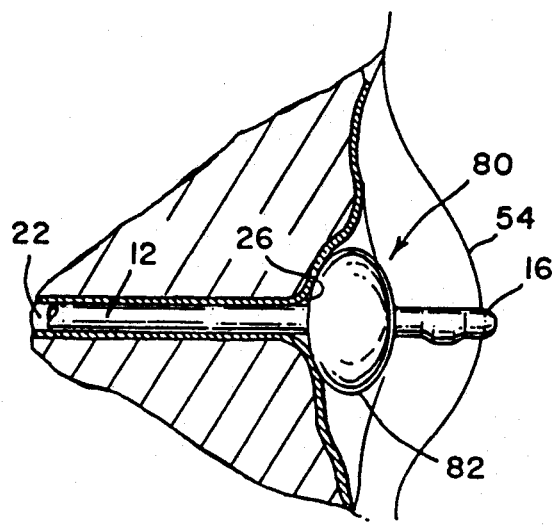

A female incontinence control device incorporating one embodiment of the invention is generally indicated by the reference number 10 in FIGS. 1 to 4.

The device 10 includes a conduit or tube 12 having an inlet opening 14 at one end (FIG. 1) and an outlet opening 16 at an opposite end. The openings 16 and 14 communicate through a lumen 18 (FIG. 2) formed within the tube 12. The lumen 18 constitutes a drainage passage for urine from the bladder 20 of a user to the outlet opening 16 of the conduit 12.

To prevent migration of the conduit 12 relative to the urethra 22 of the user, anchoring structures larger than the diameter of the urethra are located at a neck portion 24 of the bladder 20 and at and the distal urethral orifice 26. The anchoring structure at the bladder neck 24 includes a conventional inflatable bladder balloon 28 provided on the conduit 12 adjacent the inlet opening 14. The balloon 28 is inflated through a lumen 30 that communicates at one end with the interior of the balloon 28. The lumen 30 does not communicate with the lumen 18.

An inflation check valve, generally indicated at 32, is provided at the opposite end of the lumen 30 and is accessed through a passage 34. Inflation fluid is thus introduced into the balloon 28 through the check valve 32 by inserting a known inflation device such as a needle (not shown) into the passage 34. The needle infuses fluid past a spring biased check valve ball 35 to inflate the balloon 28.

The inflation check valve 32 is contained within an enlarged peripheral bulge 36 which functions as an anchoring structure that prevents migration of a distal portion 38 of the conduit 12 into the urethra 22.

Although the anchoring structures of the device 10 are represented by the inflatable balloon 28 and the enlarged bulge 36, it will be apparent to those skilled in the art that other suitable known anchoring structures can be employed, such as for example, non-inflatable collapsible bulges, Malecot tips and spirals. Inflatable balloons can be inflated with water, saline or other suitable liquids or can contain a silicone foam which is inflated with air. Removal of air collapses the foam and the balloon.

Referring to FIGS. 2 and 4 a manually controllable valve generally indicated at 40, is provided at the distal portion 38 of the conduit 12, intermediate the enlarged bulge 36 and the outlet opening 16. The valve 40 includes a generally semi-spherical valve seat 42 and a movable ball 44.

The ball 44 is shown in a valve open position in FIG. 2, and in a valve closed position in FIG. 4. The valve 40 also includes a first set of protrusions 46 molded on the interior surface of the conduit 12 at approximately 120 degree intervals as shown in FIG. 3. A second set of protrusions 48, structurally similar to the first set of protrusions 46, is axially spaced a predetermined amount from the first set 46. The protrusions 46 and 48 serve as detents to normally hold the ball valve 44 therebetween, as shown in FIG. 2, when the valve 40 is in the open condition.

When a user squeezes the distal end portion 38 of the conduit 12 at the left side of the ball 44, as viewed in FIG. 2 and as shown by arrows A—A in FIG. 4, the ball 44 is shifted from the valve open detent position of FIG. 2 to the valve closed detent position of FIG. 4. Thus the ball 44, in progressing to the valve closed detent position passes through an opening 50 defined by an annular protrusion 52 formed on the interior surface of the tube 12. The ball 44 is then locked between the annular protrusion 52 and the semi-spherical valve seat 42 to close off the lumen 18.

In order to move the ball 44 away from the valve seat 42, the conduit 12 is squeezed on the right side of the ball 44 as viewed in FIG. 4, between the outlet opening 16 and the ball seat 42. It will be noted that the conduit 12 is formed of a suitable flexible biocompatible material such as silicone and constructed such that the forces necessary to accomplish shifting of the ball 44 from the valve open detent position of FIG. 2 to the valve closed detent position of FIG. 4 and vice versa can be easily applied by the user.

In preparation for use, the device 10 is initially inserted into the user's urinary tract 22 in a known manner similar to that in which a Foley Catheter is inserted. After insertion of the device 10, a known syringe or inflation connector (not shown), for example a Davis Catheter may be used to inject inflation fluid directly into the inflation lumen 30, via the passageway 34 and valve 32 to inflate the bladder balloon 28.

The device 10 is thus installed as schematically shown in FIG. 1 with the valve 38 in the valve closed detent position of FIG. 4. Thus urine that collects in the bladder 20 enters the conduit 12 via the inlet opening 14 and is blocked from discharge through the outlet opening 16 by the closed valve 40. The closed valve 40 permits urine to accumulate in the bladder 20 by preventing urine flow and thus maintains continence for the user.

Preferably the entire device 10 is located within the user's body so that the outlet opening 16 is positioned within and adjacent to or distal to the labia majora 54 of the user and the valve means 38 is positioned generally adjacent or distal to the labia minora 52 of the user.

When desired, the user may insert her thumb and forefinger between the labia majora 54 (if valve is situated between labia majora) to squeeze the distal end portion 38 of the conduit 12 and move the ball 44 from the valve closed detent position of FIG. 4 to the valve open detent position of FIG. 2. Accordingly, urine can flow from the bladder 20 into the conduit inlet opening 14 and through the lumen 18 past the valve 40 for discharge through the outlet opening 16.

After urination is completed the user again squeezes the distal end portion 38 to move the ball 44 from the valve open position of FIG. 2 to the valve closed position of FIG. 4. Continence is thus maintained without the need for external collection devices or actuating structures that extend from the body. Under this arrangement the user can urinate at her convenience provided she actuates the valve 40 from the detent closed position to the detent open position.

To remove the device 10, the end of the conduit 12 is cut with a scissor upstream of the inflation valve 32 in order to bleed the inflation lumen 30 and deflate the bladder balloon 28. The conduit 12 may then be withdrawn from the urethra 22 and discarded.

If desired, the device 10 can be incorporated with a closed inflation system (not shown), wherein the bladder balloon 28 communicates with an inflation reservoir balloon (not shown). The reservoir balloon is connected to the inflation passage 34 for communication with the check valve 32. The inflation reservoir eliminates the need for a syringe or inflation connector (Davis Catheter). Pressure on the reservoir balloon after installing the device 10 in the urethra 22 causes the check valve 32 in the inflation lumen 30 to open, allowing the bladder balloon 28 to inflate. The inflation reservoir can be removed after installation is completed. In this variation of the device 10 removal is also accomplished by cutting the inflation lumen 30, for example with a scissor, proximal to and upstream of the check valve 32.

Another embodiment of the female incontinence control device is generally indicated by the reference number 60 in FIG. 5. The device 60 includes a disk and ratchet anchoring structure, shown generally at 62, to replace the enlarged bulge 36 of the device 10. In order to inflate the balloon 28 the conduit 12 is provided with a protrusion 74 of only limited axial and radial extent sufficient to accommodate the inflation check valve 32 and the passageway 34 leading thereto. The device 60 includes a valve 40 and is otherwise structurally similar to the device 10.

The disk and ratchet anchoring structure 62 includes a plurality of axially spaced, circumferentially extending ribs 64, 66 and 68, and depressions 70 formed on the outer periphery of the conduit 12 between the ribs 64, 66 and 68. An annular disk member 72 in the shape of a dish encircles the conduit 12 to cooperate with the ribs 64, 66 and 68, and the depressions 70.

The annular disk member 72 has an internal diameter 74 that is slightly greater than the external diameter of the conduit 12 at the depressions 70 but is less than the external diameter of the conduit 12 at the ribs 64, 66 and 68. Under this arrangement a selected length of the conduit 12 can be positioned between the bladder balloon 28 (FIG. 1) and the disk member 72 to correspond with the length of the urethra 22. The disk member 72 is preferably positioned within the labia majora.

The conduit 12 and the disk 72 are made of a resilient elastomeric biocompatible material such as silicone. The disc 72 is preferably relatively flexible in comparison to the conduit 12 to facilitate axial positioning of the disk 72 along the conduit 12 in order to change the position of the disk 72 relative to the ribs 64, 66 and 68 and the depressions 70. Installation and operation of the device 60 is accomplished in a manner similar to that previously described for the device 10.

Still another embodiment of the female incontinence device is generally indicated by the reference number 80 in FIG. 7. The device 80 includes the drainage control valves 40 of the devices 10 and 60 and differs from the device 60 by provision of a second inflatable balloon 82 at the urethral orifice 26 to replace the disk and ratchet structure 62. The device 80 is otherwise structurally similar to the device 60.

The urethral orifice balloon 82 is inflated through an inflation valve and inflation lumen (not shown) identical to the bladder balloon inflation valve 32 and the bladder balloon inflation lumen 30 of the device 10. The lumen and inflation valve for the urethral orifice balloon 82 are separate from and noncommunicable with the bladder balloon inflation lumen and the urinary drainage lumen.

The urethral orifice balloon 82 is axially located on the conduit 12 a predetermined distance from the bladder balloon 28. The preferred positioning results in a location of the inflated balloon 82 outside the urethral orifice 26 for accommodation within the labia majora 54 to prevent migration of the installed device 80 toward the bladder 20. Such location of the urethral orifice balloon 82 also helps prevent inadvertent withdrawal of the device 80 from the urethra. Installation and operation of the device 80 is accomplished in a manner similar to or obvious from the installation and operation procedures described for the device 10.

A further embodiment of the female incontinence control device is generally indicated by the reference number 90 in FIG. 6. The device 90 includes a conduit 92 having a proximal end portion 94 that aligns with and projects slightly into the urethra 22 at the distal urethral orifice 26. An opposite distal end portion 96 of the conduit 92 is identical to the distal end portion 38 of the device 10 and includes the outlet opening 16 and the drainage control valve 40.

The conduit 92 also includes an enlarged flexible flange 100 that extends about the distal urethral orifice 26 and is adhered to the meatus (not shown) by a suitable known biocompatible gel such as a tacky silicone gel (not shown). The flange 100 extends laterally about the urethral orifice 26 and is in engagement with the labia minora (not shown) and the labia majora 54. The tacky silicone gel also adheres the outer portion of the flange 100 to the labia majora 54 and thus helps retain the device 90 in a position wherein the flange 100 and the conduit 92 close the urethral orifice 26.

When the valve 38 is manually actuated to an open position in the manner previously described for the device 10, urine is permitted to drain from the distal opening 16. Since the device 90 is held in place at the urethral orifice 26 by a gel and is not otherwise physically locked in the urethra, removal thereof is a simple procedure of eliminating the gelatinous bond. Operation of the device 90 is accomplished in a manner similar to or obvious from the operational procedures described for the device 10.

Another embodiment of the female incontinence control device is generally indicated by the reference number 110 in FIG. 10. The device 110 includes a urine collecting member 112 supported at a proximal end of a conduit 114 similar to the distal end portion 38 of the conduit 12 for the device 10. The urine collecting member 112 includes a urine inlet opening 116 that communicates with the conduit 114.

The urine collecting member 112 also includes a pericup portion 118 and a vaginal engaging portion 120. A relatively thin, flexible flange portion 122 is formed opposite the vaginal engaging portion 120 and extends radially beyond the conduit 114.

The conduit 114 incorporates the drainage control valve 40 and the outlet opening 16 previously described for the device 10.

Figure 8:
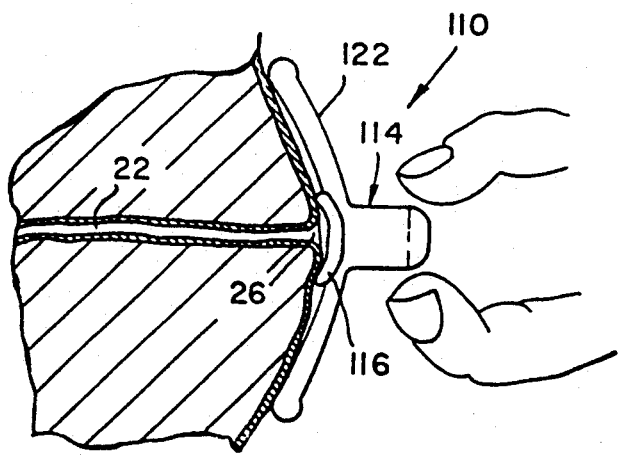
Figure 9:
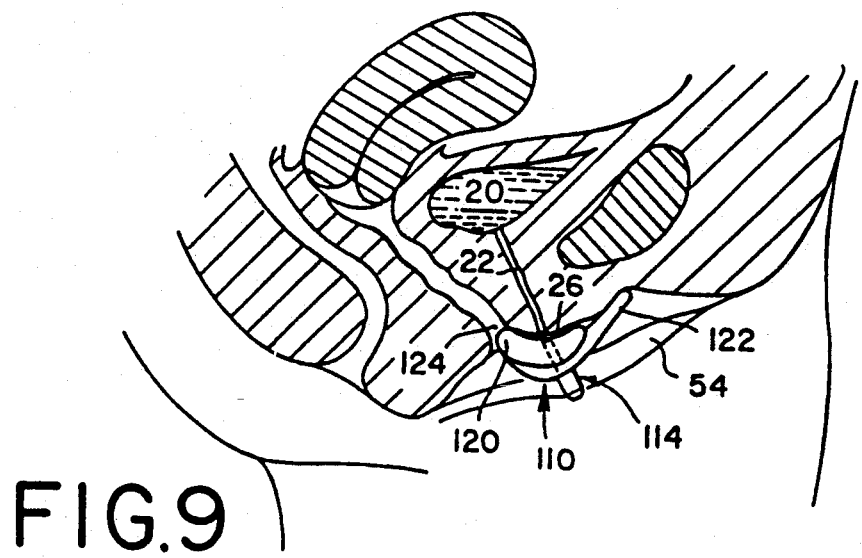
FIG. 9 is a simplified schematic view of the FIG. 8 embodiment in position within the female anatomy.

Referring to FIGS. 8 and 9, the flange portion 122 of the device 110 is adhered to the meatus and to the labia majora 54 as well as the labia minora (not shown) with a suitable known tacky silicone gel to help maintain the device 110 in position at the urethral orifice 26. Under this arrangement, the pericup portion 118 of the urine collecting member 112 is adhered about the distal urethral orifice 26, as shown in FIG. 8, and the vaginal portion 120 of the urine collecting member 112 is adhered to and anchored within the vaginal opening 124.

Since the device 110 is held in place at the urethral orifice 26 by a gel and is not otherwise physically locked in the urethra, removal thereof is a simple procedure of eliminating the gelatinous bond. Operation of the device 110 is accomplished in a manner similar to or obvious from the operational procedures described for the device 10.

Another embodiment of the female incontinence control device is generally indicated by the reference number 130 in FIG. 11. The device 130 differs from the device 10 in its structure of a manually controllable drainage valve 132 that replaces the manually controllable drainage valve 40. The device 130 is otherwise identical to the device 10.

The drainage valve 132 omits the annular protrusion 52 of the device 10 but includes the axially spaced protrusions 46 and 48 and the semispherical valve seat 42. The semispherical valve seat 42 is spaced a predetermined distance from the protrusions 48 such that the ball 44 can be detented in a valve closed detent position between the protrusions 48 and the valve seat 42.

The device 130 is otherwise similar to the device 10 and operates in a manner similar to that previously described for the device 10.

A further embodiment of the female incontinence control device is generally indicated by the reference number 140 in FIG. 12. The device 140 differs from the device 130 in the structural arrangement of an inflation check valve 142. The inflation check valve 142 axially aligns with the inflation lumen 30 within the confines of the conduit 12.

The components of the check valve 142 are similar to the components of the check valve 32. A passage 144 to the check valve 142 has an entry portion 146 that is angularly offset from the axis of the valve 142. The valve 142 is otherwise operationally similar to the valve 32 of the device 10. Installation and operation of the device 140 is accomplished in a manner similar to or obvious from the installation and operation procedure described for the device 10.

It should be noted that the drainage control valve 132 can be substituted for the drainage control valve 40 in any previously described embodiments that include the drainage valve 40.

Another embodiment of the female incontinence control device is generally indicated by the reference number 150 in FIGS. 13 and 14. The device 150 includes a conduit 152 with a lumen 154 similar to the lumen 18. The device 150 also includes an inflation lumen 156 similar to the inflation lumen 30.

The inflation lumen 156 includes a suitable known sealant material 158 that can be penetrated by an inflation needle (not shown) through an access passage 159 for inflation of a bladder balloon (not shown) similar to the bladder balloon 28. The sealant maintains a leaktight seal of the inflation lumen 30 after the bladder balloon is inflated and the inflation needle is withdrawn.

The device 150 further includes a valve means 160 provided in a block portion 162. The block portion 162 includes a passageway 164 joined to the lumen 154 through an offset passage 166. The passageway 164 includes a resilient valve seat 168 for a ball valve member 170, and an outlet opening 172 that is closed off when the ball valve 170 is in the valve seat 168. The valve means 160 also includes a resilient spherical valve seat 174 laterally spaced from the valve seat 168 for detenting the ball valve 170 into a valve open position.

As viewed in FIG. 13, pressure applied to the block portion 162 at the valve seat 168 below the ball valve 170 causes the ball valve 170 to shift into the valve seat 174 to detent the ball valve member 170 in a valve open detent position. The ball valve 170 is shifted from the valve open detent position in the valve seat 174 to the valve closed position 168 by squeezing the block portion 162 above the valve open valve seat 174.

The device 150 can also include a distal anchoring device on the conduit 152 for positioning at the urethral orifice 26, similar to the inflatable balloon 82.

It will be noted that the device 150 can provide for an increased flow of urinary fluid through the lumen 154 for discharge from the outlet opening 170 because the ball valve 168 can be substantially removed from the passageway 164 which leads to the outlet opening 170. Installation and operation of the device 150 is accomplished in a manner similar to or obvious from the installation and operation procedure described for the device 10.

Although the various embodiments of the invention include ball valves, it will be apparent to those skilled in the art that various other valve designs can be used which are operable to maintain the valve in a valve open position when desired and a valve closed position when desired. For example, a mitre valve or a duck bill valve can be used to manually hold the valve in a valve open position and other suitable known arrangements can be used to maintain the valve in a valve closed position.

Some advantages of the present invention evident from the foregoing description include a manually actuatable female incontinence control device that is convenient to operate by the user and does not require an external collection system. The novel arrangement of the drainage control valve in the drainage conduit enables the valve to remain entirely contained intermediate the labian fold and the meatus or distal to the labia. Thus the user can be relatively free of impediment in carrying out normal activities as compared with known devices that require the use of external collection systems or components that extend away from the labia. A further advantage of the present invention is the facility of the user in obtaining a urinary discharge whenever it is convenient to do so and to maintain continence at other times.

The catheter could be coated with an antimicrobial coating to further reduce the risk of urinary tract infection In view of the above, it will be seen that the several objects of the invention are achieved and other advantageous results attained.

As various changes ca be made in the above constructions and method without departing from the scope of the invention, it is intended that all matter contained in the above description or shown in the accompanying drawings shall be interpreted as illustrative and not in a limiting sense.

What is claimed is:

1. An incontinence device for a human female comprising a flexible conduit having inlet and outlet openings and a ball valve means for controlling flow of urine past the outlet opening, said ball valve means being shaped to be positioned within the labia majora of a female, with said conduit sealingly engaging the urinary tract of the female to receive substantially all of the urinary fluids which drain from the bladder, so that said ball valve means, when closed, permits accumulation or urinary fluids in the urinary tract and, when open, allows the urinary fluids to pass through the conduit for discharge from the outlet opening, and said ball valve means being selectively manually actuatable by squeezing said flexible conduit at said control ball valve means to allow accumulated urinary fluids to be drained from the urinary tract.

2. An incontinence device comprising a conduit having an inlet opening for receiving urinary fluid from the bladder, an outlet opening for discharging urinary fluid, a longitudinal axis extending between said inlet and outlet openings, and a conductive section intermediate said inlet and outlet opening for conducting said urinary fluid from said inlet opening to said outlet opening; means for holding said conduit in a predetermined position relative to the urethra, said holding means including a positioning member provided on said conduit for disposition of said holding means between the urethral orifice and the labia majora, said positioning member having a predetermined cross sectional magnitude greater than the magnitude of the urethral orifice to prevent migration of said conduit from said predetermined position toward said bladder; an outlet section of said conduit being defined from said positioning member to said outlet opening; valve means provided in said conduit at said outlet section for controlling the flow of urinary fluid through said conduit means for discharge through said outlet opening, said valve means being axially movable within said conduit and manually actuatable at said outlet section from a closed position to an open position by squeezing said conduit at said value means to selectively control discharge of urinary fluid from said outlet opening and holding means within said conduit for holding said valve means in said closed position or said open position.

3. The incontinence device according to claim 2 wherein said valve means is deformable and actuatable from said closed position to said open position by manually deforming the outlet section of said conduit.

4. A method of controlling female incontinence, comprising providing a conduit having inlet and outlet openings and a control valve for controlling flow of urine past the outlet opening, positioning at least the inlet opening and valve portion of the conduit within the labia majora of a female, with the inlet opening of the conduit sealingly engaging the urinary tract of the female to receive substantially all of the urinary fluids which drain from the bladder, so that the valve, when closed, permits accumulation of urinary fluids in the urinary tract and, when open, allows the urinary fluids to pass through the conduit for discharge from the outlet opening, and selectively manually opening the valve by squeezing the conduit at the control valve to allow accumulated urinary fluids to be drained from the urinary tract.

5. A method of controlling female incontinence according to claim 4, wherein the step of positioning at least portions of the conduit within the labia majora includes positioning the entire conduit within the labia majora so that when the valve is opened, urinary fluids pass out of the outlet opening of the conduit within the labia majora and then pass through the labia majora during their discharge from the urinary tract.

6. An incontinence device for a female, comprising:
(a) conduit means having inlet and outlet openings for receiving, conducting and discharging urinary fluids from the bladder; and a longitudinal axis extending between said inlet and outlet openings;
(b) means secured to said conduit means for holding said conduit means in a predetermined position relative to the urethra such that said inlet opening is adapted to receive urinary fluid which drains from the bladder toward the urethra and such that said outlet opening is positioned outside the urethra;
(c) valve means provided within said conduit means and outside the urethra operable for manual activation reversibly between a closed position and an open position by squeezing said conduit means at said valve means for selectively controlling the flow of urinary fluid through said conduit means for discharge through said outlet opening, said valve means being axially movable within said conduit means; and
(d) holding means within said conduit means for holding said valve means in said closed position or said opening position.

7. An incontinence device according to claim 1 wherein said conduit means is deformable at said valve means to permit manual deformation of said conduit means to actuate positioning of said valve means into a valve open position or a valve closed position.

8. An incontinence device according to claim 1 where, and said valve means comprises a ball valve having a ball axially moveable within said conduit means, between a valve-open position and a valve-closed position, upon manual manipulation of said conduit means.

9. An incontinence device according to claim 8 wherein said holding means for said valve means include detent means for holding said ball valve in said valve open position or said valve closed position.

10. An incontinence device according to claim 9 wherein said conduit means is deformable at said valve means to permit manual deformation of said conduit means to actuate positioning of said valve means into said valve open position or said valve closed position.

11. An incontinence device according to claim 6 wherein said valve means comprises a ball valve having a ball radially movable within said conduit means between a valve open position and a valve closed position, upon manual manipulation of said conduit means.

12. An incontinence device according to claim 6, wherein said conduit means is of a predetermined size for entire self containment within the labia majora.

13. An incontinence device according to claim 7, including means carried by said conduit means adjacent said valve means for preventing migration of said valve means into the urethra, said migration preventing means permitting positioning of said inlet opening adjacent the externally communicating orifice.

14. An incontinence device according to claim 13 wherein said conduit means includes a conduit and a wall-forming member projecting from said conduit, said wall forming member having an end surface facing said inlet opening that surrounds said inlet opening, and wherein said holding means comprises an adhesive gel provided on the end surface for contact with the urethral meatus.

15. An incontinence device according to claim 12 wherein said holding means comprises a flange-like member contoured to fit between the urethral meatus and the labia minora to permit positioning of said inlet opening adjacent the urethral orifice.

16. An incontinence device according to claim 15 wherein said holding means further includes an adhesive gel provided on said flange-like member.

17. An incontinence device according to claim 1 wherein said conduit means includes a first conduit portion containing the inlet opening and an elongated portion adapted to extend through the urethra to position the first conduit portion within the bladder, and wherein said holding means includes an expansible diaphragm member carried by the first conduit portion adjacent said inlet opening and inflatable within the bladder to prevent withdrawal of the first conduit portion from the bladder.

18. An incontinence device according to claim 17 wherein said conduit means includes a second conduit portion containing the valve means and wherein said holding means includes means provided on said second conduit portion for preventing migration of said valve means into the urethra.

19. An incontinence device according to claim 18 wherein said migration preventing means comprises an enlarged portion of said conduit means, said enlarged portion being of a predetermined size greater than the size of the externally communicating urethral orifice.

20. An incontinence device according to claim 18 wherein said conduit means includes means for adjusting the distance between said enlarged portion of said conduit means and said expansible diaphragm.

21. An incontinence device according to claim 20 wherein said conduit means comprises a resilient material and said adjusting means comprises a plurality of axially spaced, circumferential ribs and depressions at said second conduit portion, and wherein said enlarged portion includes a deformable annular, flexible disk member having an internal diameter greater than the external diameter of said conduit means at said depressions but less than the diameter of said conduit means at said ribs to permit selective axial positioning of said disk member on said second conduit portion at an elected depression, to provide for adjustability of the length of the conduit means that is positioned between the expansible diaphragm and the disk member to correlate with the length of the urethra.

22. An incontinence device according to claim 18 wherein said migration preventing means comprises an expansible diaphragm member at said second conduit portion.

23. An incontinence device according to claim 18 wherein said second conduit portion is of a predetermined length to permit containment of said valve means intermediate the externally communicating urethral orifice and the labia majora.

* * * * *